(12) United States Patent
Hobbs

(10) Patent No.: US 6,273,929 B1
(45) Date of Patent: Aug. 14, 2001

(54) EXTRUSION PROCESS

(75) Inventor: David G. Hobbs, Research Triangle Park, NC (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/296,613

(22) Filed: Apr. 23, 1999

Related U.S. Application Data

(60) Provisional application No. 60/082,876, filed on Apr. 24, 1998.

(51) Int. Cl.$^7$ .............................. B02C 19/00; C05G 5/00
(52) U.S. Cl. ..................... 71/64.03; 71/64.06; 264/15; 264/140; 264/141; 424/408; 514/952
(58) Field of Search ................... 71/64.02, 64.03, 71/64.06; 424/405, 489, 408; 264/15, 140, 141; 514/952

(56) References Cited

U.S. PATENT DOCUMENTS

| | | |
|---|---|---|
| 4,983,390 | 1/1991 | Levy . |
| 5,075,058 | 12/1991 | Chan et al. . |
| 5,151,264 | 9/1992 | Samain et al. . |
| 5,443,764 | 8/1995 | Lloyd et al. . |
| 5,643,593 | 7/1997 | Fersch et al. . |
| 5,705,193 | 1/1998 | Bourgogne et al. . |
| 5,714,157 | 2/1998 | Sandell et al. . |
| 5,846,903 * | 12/1998 | Lloyd ..................................... 264/15 |
| 6,051,533 * | 4/2000 | Kajikawa et al. ................... 504/206 |
| 6,063,313 * | 5/2000 | Briskin et al. ......................... 264/15 |
| 6,083,875 * | 7/2000 | Sato et al. ............................ 504/127 |

FOREIGN PATENT DOCUMENTS

| | | |
|---|---|---|
| 0 448 538 A1 | 9/1991 | (EP) . |
| 87982 * | 6/1994 | (JP) . |
| 94/09627 | 5/1994 | (WO) . |

* cited by examiner

*Primary Examiner*—Wayne Langel
(74) *Attorney, Agent, or Firm*—Nixon & Vanderhye P.C.

(57) ABSTRACT

The present invention provides an improved process for making extruded granules containing an agriculturally active ingredient.

16 Claims, No Drawings

EXTRUSION PROCESS

This application claims the benefit of U.S. Provisional Application No. 60/082,876, filed Apr. 24, 1998.

This invention relates to formulations of agricultural chemicals, minerals and other substances. It is more particularly concerned with the methods of preparing water dispersable granules containing such substances. The present invention provides an improved method of forming granules containing agricultural chemicals.

Agricultural chemicals are formulated in a number of ways, e.g. as large granules (prills) for direct application to soil, pasture or crops, emulsifiable concentrates, liquid flowable concentrates and wettable powders which are normally diluted with water for application. Liquid flowables and wettable powders comprise the majority of the agricultural chemical formulations sold throughout the world. The former are aqueous suspension and while generally giving satisfactory performance, can settle out of suspension during storage requiring vigorous mixing to re-suspend. Because of the high water content (generally around 50%), packaging and freight costs are increased.

Wettable powders are generally produced by first blending the technical grade chemical, with surfactants (wetting and dispersing agents), fillers and possibly other ingredients. The mixture is then passed through an air-mill or other suitable milling device to reduce the size of the additives as well as produce an intimate mixture of the components.

The resultant wettable powder is generally very bulky and becomes air borne readily. This can be hazardous to the user in the case of irritant or toxic materials.

Water dispersible granules (also known as dry flowables) containing agricultural chemicals are designed to disperse readily in water and remain in suspension, i.e. perform as well as liquid flowables and wettable powders when prepared for spray application to soil or plants. One desirable aspect of dry flowable materials is their applicability to solid chemicals of low water solubility. The usual method of producing "dry flowables" is to convert the active agent to a wettable powder formulation by blending and milling the ingredients of the formulation. The resultant powder is then converted to a granule by agglomeration using a pan-granulator or similar device using water or water containing a binder. This is a rather crude process and control of granule size is difficult to achieve.

Water dispersible granules may also be made by mixing the desired ingredients of the granules into an extrudable form, extruding the mix and then drying, if required, the extruded product. Mechanical agitation may or may not be required or preferred to adjust the size of the granules. Extrusion methods practiced in the art may also include mixing water with the composition prior to extrusion.

U.S. Pat. No. 5,443,764 provides a method for forming a water dispersible granule comprising mixing the desired ingredients of the granules in the presence of water to form an extrudable wet mix, extruding the wet mix, and rolling the wet extrusions to break down the extrusions to form granules, and optionally drying the granules.

The present inventor has discovered that especially for active ingredients of extremely low water solubility (i.e., less than about 10 grams per liter water or 1%), the extrusion process may surprisingly be made more efficient, without reduction in biological effect of the active ingredient, if an organosilicone surfactant is added in minor amounts to the active ingredient mixture prior to extrusion.

The present invention also provides an extrusion process and extrudable and extruded compositions which contain crystalline materials (i.e., active and/or inert ingredients) which have a glass transition temperature ($T_g$) of less than about 65° C., alternatively, less than about 75° C. By lowering the temperature of operation of the extrusion process, the present invention makes it possible to extrude materials, such as active and/or inert ingredients which have a glass transition temperature ($T_g$) of less than about 65° C., alternatively, less than about 75° C., more efficiently, while maintaining the crystalline structure of the active and/or inert material. Previously, extrusion of such active and/or inert materials at higher temperatures created amorphous solids which deteriorated the water dispersability of the extruded product. Accordingly, the present invention provides improved extruded water dispersible products.

The organosilicone of the present invention is preferably solubilized in water used to create the "dough" consistency required for extrusion, as opposed to being added to the premix powder directly.

The ingredients of the extrudable composition of the present invention will generally contain one or more active chemical components which may be liquid or solid at ambient temperature and either of an insoluble or water soluble type.

Typically the active chemical component comprises from 1 to 99%, preferably from 20 to 95% by weight of the dry weight of the composition, more preferably about 50 to 80% by weight of the dry weight of the composition.

The process of the invention may be performed using a wide range of active ingredients.

Examples of active ingredients include agricultural chemicals such as pesticides, herbicides, fungicides, insecticides and fertilisers; pigments; dyestuffs; pharmaceuticals and trace elements.

Examples of herbicidal active ingredients may be selected from one or more of: benzo-2,1,3-thiadiazine-4-one-2,2-dioxides and such as bentazon; hormone herbicides such as MCPA, dichlorprop, MCPB and mecoprop; 3-[4-(4-halophenoxy)phenyl]-1,1-dialkylureas such as chloroxuron; dinitrophenols and their derivatives, for example, DNOC, dinoterb and dinoseb; dinitroaniline herbicides such as dinitramine, nitralin and trifluralin; phenylurea herbicides such diuron and fluometuron; phenylcarbamoylphenylcarbamates such phenmedipham and desmedipham; 2-phenylpyridazin-3-ones such as as pyrazon; uracil herbicides such as lenacil, bromacil and terbacil; triazene herbicides such as atrazine, simazine and aziproptryne; 1-alkoxy-2-alkyl-3-phenylurea herbicides such as linuron, monolinuron and chlorobromuron; pyridine herbicides such as clopyralid and picloram; 1,2,4-triazin-5-one herbicides such as metamitron and metribuzin; benzoic acid herbicides such as 2,3,6-TBA, dicamba and chloramben; anilide herbicides such as balachlor, alachlor, propachlor and propanil; dihalobenzonitrile herbicides such as dichlobenil, bromoxynil and ioxynil; haloalkanoic herbicides such as dalapon and TCA; diphenylether herbicides such as fluorodifen and bifenox; N-(heteroarylaminocarbonyl) benzenesulphonamides such as DPX 4189; Aryloxyphen oxyproprionate herbicides such as fluazifop and diclofop; cyclohexane-1-3-dione derivatives such as alkoxydim-sodium and tralkoxydim; bipryidylium herbicides such as paraquat and diquat; organoarsenical herbicides such as MSMA; amino acid herbicides such as glyphosate; and other herbicides such as dipenamid and naptalam.

Preferred herbicides include diuron, atrazine, simazine, cyanazine, oryzalin, fluometuron, methazole, metoxuron and hexazinone.

Examples of fungicides include imazalil, benomyl, carbendazim (BCM), thiophanate-methyl, captafol, folpet, captan, sulphur, carbamates, dithiocarbamates, phenyl-tin compounds, carbathiins, dicarboximides (including iprodione, vinclozolin, procymidone), copper oxychloride, triforine, dodemorph, tridemorph, dithianon, pyrazophos, binapacryl, quinomethionate, panoctine, furalaxyl, aluminium tris(ethylphosphonate), cymoxanil, ethirimol, dimethirimol, fenarimol, fenpropidin, fenpropimorph, propiconazole, bupirimate, metalaxyl, ofurace, benalaxyl, oxadixyl, chlorothalonil, metaxanine, triazole derivatives such as triadimefon, triadimenol, diclobutrazol, flutriafol and penconazole and ergosterol-synthesis inhibiting fungicides.

Preferred fungicides for use as an active ingredient may include captan, thiram, mancozeb, dichlofluanid, metiram and vinclozolin.

Examples of insecticides which may be used as an active ingredient may include pyrethroids such as cypermethrin organophosphorus insecticides, pirimor croneton, dimethoate, metasystox, and formethion.

Examples of pigments may include any one of the wide range of powdered pigments or mixtures thereof. Suitable pigments may be chosen from diverse classes including: organic pigments of the anthraquinone, azoprophine, azo, dioxazine, naphthalenetetracarboxylic acid, perylenetetracarboxylic acid, polycyclic, quinacridone and thioindigo series, specific examples of which may be found in the Colour Index, 2nd edition; and inorganic pigments such as the colored pigments of the alkaline earth, antimony, cadmium, chromium, copper, iron, lead, ultramarine and zinc group (Kirk-Othmer, Encyclopedia of Chemical Technology 15, 496–516 (1968), white pigments such as titanium dioxide, zinc oxide, zinc white lithopones (Kirk-Othmer, Encyclopedia of Chemical Technology, 15, 517–541 (1968)); Copper phthalocyanine pigments such as those referred to in the Colour Index 2nd edition as Pigment Blue; and carbon black.

Examples of dyestuffs may include anthraquinone dyes, azo dyes, methine dyes and naphthoquinone dyes.

In addition to the active ingredient component the ingredients will include at least one organosilicone surfactant component and may contain other surfactants and optionally other components such as a filler component to provide the desired active ingredient content and/or a binding agent and/or a dispersant, such as, for example, lignosulfonate, naphthalene formaldehyde condensate, kraft lignosulfonate, and EO/PO (ethylene oxide/propylene oxide) block copolymer (such as Pluronic™ and Plurafac™ surfactants, from BASF).

The organosilicone surfactant component of the present invention is preferably a silicone glycol copolymer which is nonionic, has an HLB (Hydrophilic/Lipophilic Balance) number in the range of about 5–13, alternatively, an HLB of 5–11 or preferably an HLB of 5–8 and reduces the surface tension of the composition without being toxic to the plants to be treated. The organosilicone surfactant of the present invention is used in an amount of between 0.001 and 0.4%, alternatively, in an amount of 0.001 to 0.01%, by weight of the dry weight of the preextruded composition. The present inventor has discovered that more than this amount of the organosilicone surfactant will no longer be effective at reducing the surface tension of the preextruded mix and will, in fact, detrimentally effect the extrusion process, and making it difficult and less economical to produce a dry granule. The method of the present invention, which includes addition of an organosilicone surfactant in the preextrusion mix of an extrudable agricultural product, allows for a reduction in water for extrusion, thus surprisingly leading to energy and material savings in manufacturing the agricultural granules described herein. Moreover, the present invention provides an improved extrusion process in that there is less abrasion produced at the extrusion die surface, as evidenced by a reduction in die face temperature. Moreover, because there is less water needed in the extrusion process, the active component of the compositions according to the present invention are not subjected to the increased temperatures for sustained time which is required to remove the excess water in traditional extrusion processes. Further, the improved process of the present invention should be widely applicable and not require re-registration of agricultural products as only a minor amount of organosilicone surfactant is being added.

Examples of organosilicone surfactants useful in the present invention include, for example, nonionic siliconeglycol copolymers, such as those available from SILWET (Witco OSi Specialties Group, One American Lane, Greenwich, Conn.), including SILWET L-77 (silicone polyalkylene oxide-modified dimethyl polysiloxane)(CAS: 27306-78-1), SILWET L-7210, L-7220, and L-7230 (CAS: 68937-55-3) and as described in Adjuvants for Agrichemicals Ed. Foy, CRC Press (1992), and nonionic silicone polyethers, such as are available from Dow Corning (Midland, Mich.), such as Sylgard 309 (2-(3-hydroxypropyl) heptamethyltrisiloxane, ethoxylated, acetate), and mixtures thereof, so long as the mixture or individual components are not phytotoxic.

One measure of phytotoxicity includes the aqueous dilution of a given pesticide to the most concentrated application spray permissible by the product's EPA registered label recommendations, and the application of this dilution to the surface of the target crop at the highest recommended pounds of active/unit area, and observing the crop for 21 days, noting any discoloration or physiological changes that are detrimental to the development of the crop.

In one embodiment of the present invention, the only surfactant present in the extrudable or extruded composition is an organosilicone surfactant, such as are described herein. Accordingly, in this embodiment, the composition contains no additional surfactant but the organosilicone surfactants as described herein.

Examples of additional surfactants of the anionic type which may be used in addition to the organosilicone surfactant of the present invention include soaps, salts of aliphitic monoesters or sulphuric acid such as sodium lauryl sulphate, salts of sulphonated aromatic compounds, for example sodium dodecylbenzenesulphonate, sodium, calcium or ammonium lignosulphonate or butylnaphthalene sulphonate, and a mixture of the sodium salts of diisopropyl- and triiso-propylnapthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters with ethylene oxide and the lecithins and phosphoxylated surfactants such as phosphorylated ethylene oxide/propylene oxide block copolymer and ethyoxylated and phosphorylated styryl substituted phenol. Additional surfactants and dispersants which may be included are those available from International Specialty Products (ISP) Europe (Research Park, Guildford, UK) Inc., such as the Agrimer® VEMA ES polymers (which are described by the manufacturer as being low molecular weight, partially neutralized, methyl vinyl ether butyl maleate copolymers and methyl vinyl ether ethyl maleate copolymers).

The composition of the present invention may contain at least one wetting agent, such as those selected from alkyl naphthalene sulfonates, phosphate esters, sulphosuccinates and nonionics such as tridecyl alcohol ethoxylate; and/or at least one dispersing agent such as those selected from the group of napthalene condensates, lignosulfonates (such as sodium ligninsulfonate), polyacrylates and phosphate esters.

A variety of fillers may be used in water dispersible granule compositions. Examples of fillers include: mineral earths and clays such as, for example, kaolin, hydrated aluminum silicate kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, sodium chloride, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Where used, the filler component typically comprises from 1 to 99% and preferably from 5 to 80% by weight, more preferably, 10 to 40%, most preferably 20–35% of the total granule composition. In one embodiment however, the granule composition may consist essentially of a filler type component such as one or more clays, an organosilicone surfactant component, a carrier, such as ammonium sulfate, a dispersant, water and the active component.

The present invention preferably involves wet-mixing the ingredients described herein and extruding the wet mix, which has dough-like consistency at the point of extrusion, that is a consistency analogous to a stiff dough produced in the bread making process. Such a dough like consistency may be provided by thorough mixing or kneading using a mixing apparatus such as pug mill, double shafted auger or an extrusion apparatus may be adapted to provide suitable mixing.

The aqueous dilution of organosilicone surfactant is preferably present in the wet mixing step of the process in a controlled amount such that there is sufficient water to mobilize the surfactant component and enable the mixture to be formed into granules by extrusion but insufficient to cause the granules to stick together and agglomerate once formed. Although the quantity of water used in a given formulation will vary it will generally be in the range of from 5 to 50 liters (preferably from 10 to 30 liters, most preferably 20 liters) of water per 100 kg of dry mix.

The order of addition and mixing of the granule ingredients is not narrowly critical. In one embodiment, for example, the dry ingredients are blended and the composition is then mixed while water is added. The water may, for example be added as a fine spray and in one embodiment one of more surfactants are added as an aqueous solution to a dry mix of the other components. The use of the above described wet mixing process further has the advantage of allowing the use of solid technical grade surfactants without the need to finely grind such surfactants.

Materials used in the process of the invention may be in a finely divided form, preferably in an air-milled form which is generally the form of technical grade chemicals supplied by manufacturers.

After thorough mixing, the composition of the present invention is extruded through suitable orifices. The size of the granules will depend upon the size of the orifices and the extruder may thus be fitted with a mesh or die selected to provide a desired size of granule. The extrusions can vary considerably in length, e.g. up to 2.5 cm or more long. One of ordinary skill will appreciate that extrudate shape is determined by the die. This is typically 2 mm or less, most typically 1 mm. The length of the noodle is typically 20 mm or less, most typically 3 to 8 mm long in the presently exemplified method.

After extruding the wet mix the wet extrusions are dried by discharge into a continuous fluid bed drier and dried to a moisture content in the range of 1–5%, preferably about 3%. The fluid bed drier used in this embodiment of the present invention preferably provides mechanical agitation to break the extruded products into individual granules of approximately the desired size. Dried granules are discharged on to a screen wherein the oversize and fines are separated, preferably, for recycle back to be milled.

Preferably at least 95% by weight of the composition will comprise granules of size such that they pass through an 8 US mesh (2.36 mm) sieve but are retained on a 300 micron sieve. In many cases it is possible to achieve over 99% of particles in this size range.

The invention is now illustrated by but in no way limited to the following example.

EXAMPLE

The following dry ingredients are weighed into a powder mixer or other suitable blender fitted with a close fitting lid, and are blended: 521 g of Vinclozolin 96% w/w (BASF AG), 50 g ammonium sulfate (BASF AG), 50 g sodium lignosulfonate (Borregaard A.S., Sarpsborg, NORWAY), 349 g hydrated aluminum silicate kaolin (Blancs Mineraux de Paris) and a mixture of SILWET L-77 and SILWET L-7230. A 1:1 blend of the two surfactants may be added to water at a dilution rate of 0.1% in the water and then 22 grams of this solution are blended with 78 grams of powdered pesticide premix (described earlier) for less than 90 seconds in a high shear mixer to make an extrudable dough that is dropped directly from the mixer into the extruder.

Alternatively, the dough may be made by blending the powdered premix with the surfactant solution in either a continuous kneader (retention time less than 20 minutes) or in a batch mixer/kneader that mixes for less than 20 minutes or in a continuous kneader/extruder system (e.g. Teledyne Readco or Bepex Extrudomixer).

The blended mixture was then extruded through a die face with 1.5 mm diameter openings at a rate close to maximum machine load. This results in further intimate mixing of ingredients, formation of a dough and extrusion of same through the die or mesh.

The extrusions so formed were discharged into a continuous or batch drier to produce granules with a residual moisture content of about 3% by weight.

The above mixture made without the organosilicone surfactant was made in an extrudable composition containing 77% dry pre-mix powder and 23% water and extruded at approximately 800 lb/hr through a 1.5 mm die. Friction at the die face raised the temperature to 65° C. and eventually contributed to die failure after 20,000 lbs. of product having been extruded. A similar composition which included the organosilicone surfactant of the present invention required only 20% moisture and a die face temperature of only 25° C., limiting the stress on the equipment/die and product. It is expected that reduced water/solvent (15–20%) could be used if greater temperatures were tolerated. An unexpected advantage of the process of the present invention is the ability to dilute the product in hard water (mineral content greater than 1000 ppm) without effecting the final product performance. Moreover, since extrusion with a lower water content is made possible by the present invention, less energy is required to dry the final product, leading to savings in time and energy. Another unexpected advantage discovered was the lowering of die face temperatures.

All references cited herein are incorporated herein by reference.

I claim:

1. In a method of extruding granules containing at least one active ingredient and at least one inactive ingredient and at least one organosilicone surfactant comprising mixing said at least one active ingredient, said at least one inactive ingredient and water to form a composition wherein the improvement comprises combining said at least one organosilicone with said water prior to said mixing and said extruding, wherein said at least one organosilicone surfactant is added in an amount in the range of greater than 0.001 to less than 0.1% by weight of the composition prior to said extrusion.

2. A method of claim 1, wherein said at least one organosilicone surfactant is a copolymer of silicone and glycol.

3. A method of claim 2, wherein said organosilicone surfactant has an HLB number in the range of 5–11.

4. A method of claim 1, wherein said method further comprises only the use of organosilicone surfactants.

5. A method of claim 1, wherein said at least one active ingredient is selected from the group consisting of a pesticide, an herbicide, a fungicide, an insecticide, a fertilizer, a pigment, a dyestuff, a trace element and a pharmaceutical.

6. A method of claim 1, wherein said at least one active ingredient is soluble in water in an amount less than 1% weight/volume.

7. A method of claim 1, wherein said at least one inactive ingredient is selected from the group consisting of a filler component, a binding agent, and a dispersant.

8. A method of claim 1, further comprising mixing at least one anionic surfactant or non-ionic surfactant or dispersant to form said composition.

9. A method of reducing the temperature of extrusion of an extruded agricultural composition comprising mixing at least one active ingredient, at least one inactive ingredient, water and at least one organosilicone surfactant to form a mixed product, and extruding said mixed product, wherein said at least one organosilicone surfactant is added in an amount in the range of greater than 0.001 to less than 0.01% by weight of the composition prior to said extrusion.

10. A method of claim 9, wherein said at least one organosilicone surfactant is a copolymer of silicone and glycol.

11. A method of claim 10, wherein said organosilicone surfactant has an HLB number in the range of 5–11.

12. A method of claim 9, wherein said method further comprises only the use of organosilicone surfactants.

13. A method of claim 9, wherein said at least one active ingredient is selected from the group consisting of a pesticide, an herbicide, a fungicide, an insecticide, a fertilizer, a pigment, a dyestuff, a trace element and a pharmaceutical.

14. A method of claim 9, wherein said at least one active ingredient is soluble in water in an amount less than 1% weight/volume.

15. A method of claim 9, wherein said at least one inactive ingredient is selected from the group consisting of a filler component, a binding agent, and a dispersant.

16. A method of claim 9, further comprising mixing at least one anionic surfactant or non-ionic surfactant or dispersant to form said mixed product.

* * * * *